(12) United States Patent
Huettenbrink et al.

(10) Patent No.: US 7,806,931 B2
(45) Date of Patent: Oct. 5, 2010

(54) OSSICLE PROSTHESIS WITH SENSITIVE TOP PLATE

(75) Inventors: Karl-Bernd Huettenbrink, Cologne (DE); Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 12/046,577

(22) Filed: Mar. 12, 2008

(65) Prior Publication Data

US 2008/0234817 A1 Sep. 25, 2008

(30) Foreign Application Priority Data

Mar. 22, 2007 (DE) .................. 10 2007 013 708

(51) Int. Cl.
*A61F 2/18* (2006.01)
(52) U.S. Cl. ........................................ 623/10
(58) Field of Classification Search ............. 623/10
See application file for complete search history.

(56) References Cited

U.S. PATENT DOCUMENTS

| 6,387,128 | B1 | 5/2002 | Kurz et al. | |
|---|---|---|---|---|
| 6,432,139 | B1* | 8/2002 | Elies et al. | ........... 623/10 |
| 6,554,861 | B2 | 4/2003 | Knox et al. | |
| 6,579,317 | B2 | 6/2003 | Kurz | |
| 2002/0045939 | A1 | 4/2002 | Kurz | |
| 2004/0162614 | A1 | 8/2004 | Steinhardt et al. | |
| 2006/0058875 | A1 | 3/2006 | Reitan et al. | |
| 2006/0161255 | A1* | 7/2006 | Zarowski et al. | ........... 623/10 |
| 2006/0271190 | A1 | 11/2006 | Reitan et al. | |

FOREIGN PATENT DOCUMENTS

| DE | 196 47 579 | 5/1997 |
|---|---|---|
| DE | 20 2005 003 782 | 6/2005 |
| EP | 1 181 907 | 2/2002 |
| WO | 02/069850 | 9/2002 |

OTHER PUBLICATIONS

Machine Translation of DE19647579 obtained from <http://ep.espacenet.com/>.*
M. W. Yung Et Al: "A Comparison of the User-Friendliness of . . ." The Journal of Laryngology & Otology, February 2002, Vol. 116, pp. 97-102. (In English).

* cited by examiner

*Primary Examiner*—David Isabella
*Assistant Examiner*—Andrew Iwamaye
(74) *Attorney, Agent, or Firm*—Michael J. Striker

(57) ABSTRACT

An ossicle prosthesis includes, at one end, a first fastening element designed as a top plate for mechanical connection with the tympanic membrane, and, at the other end, a second fastening element for mechanical connection with a component or parts of a component of the ossicular chain or with the inner ear, and a connecting element that connects the two fastening elements with each other in a sound-conducting manner; the top plate includes a radially outward annular region, a radially inward attachment region for mechanically attaching the top plate to the connecting element, and several segment elements for radially connecting the annular region with the attachment region, characterized by the fact that the segment elements are geometrically designed such that they locally emulate any localized medial motions made by the tympanic membrane, but they do not transmit the motion to distant regions of the top plate. As a result, a high level of post-operative flexibility and variability of the prosthesis, and higher-quality sound conduction through the prosthesis may be attained in a technically simple, uncomplicated, and cost-favorable manner.

39 Claims, 2 Drawing Sheets

OSSICLE PROSTHESIS WITH SENSITIVE TOP PLATE

CROSS-REFERENCE TO A RELATED APPLICATION

The invention described and claimed hereinbelow is also described in German Patent Application DE 10 2007 013 708.9 filed on Mar. 22, 2007. This German Patent Application, subject matter of which is incorporated herein by reference, provides the basis for a claim of priority of invention under 35 U.S.C. 119(a)-(d).

BACKGROUND OF THE INVENTION

The present invention relates to an ossicle prosthesis that replaces or bridges at least one component or parts of a component of the ossicular chain.

The ossicle prosthesis includes, at one end, a first fastening element designed as a top plate for mechanical connection with the tympanic membrane and, at the other end, a second fastening element for mechanical connection with a component or parts of a component of the ossicular chain or with the inner ear; it also includes a connecting element that connects these two fastening elements in a sound-conducting manner. The top plate includes a radially outer annular region, a radially inner—central, in particular—attachment region for mechanically attaching the top plate to the connecting element, and several segment elements for radially connecting the radially outer annular region with the central attachment region. A device of this type is made known in DE 20 2005 003 782 U1.

Ossicle prostheses are used in cases in which the ossicles of the human middle ear are missing or damaged, either entirely or partially, to conduct sound from the tympanic membrane to the inner ear. The ossicle prosthesis has two ends. Depending on the specific circumstances, one end of the ossicle prosthesis is fastened to the tympanic membrane, e.g., using a top plate, and the other end of the ossicle prosthesis is fastened, e.g., to the stapes of the human ossicular chain, or it is inserted directly into the inner ear. In many cases, with the known ossicle prostheses, sound conduction between the tympanic membrane and the inner ear is limited, because these known ossicle prostheses do not fully replace the natural anatomical formations of the ossicular chain.

After the prosthesis has been surgically implanted in the middle ear and the tympanic membrane has been closed, the recovery phase begins. Scars form during this period, and they produce unforeseeable forces, which can cause the prosthesis to move out of its localized position. When there is a stiff connection between the top plate and the shank, increased pressure peaks can result between the edge of the top plate and the tympanic membrane, or the graft between the tympanic membrane and the top plate. These pressure peaks can be so high that penetration or extrusion through the tympanic membrane would result. For this reason, it is very helpful for the prosthesis to have a certain amount of post-surgical mobility, so that the top plate can automatically adapt, post-operatively, to the position of the tympanic membrane.

Since, in addition, the unique anatomical features of the ear, such as the position, shape and size of the stapes, incus, hammer and tympanic membrane vary, it is very advantageous when ossicle prostheses are not designed to be rigid, but rather that they have a certain amount of flexibility or variability.

To attain this level of flexibility/variability, it is known to use various fastening and attachment devices for ossicles that have elastic parts and/or joints. A hinged connection of this type between a fastening element which can be installed on the base of stapes and the longitudinal shank is described in EP 1 181 907 B1, and is offered by the applicant under the trade mark "Ball-Joint".

A further complication that occasionally arises is caused by inadequate ventilation of the middle ear space and the associated inflammation, tumor formation, adhesions in the region of the tympanic membrane, and stiffening thereof. When the eustachian tube malfunctions, for example, under pressure may form in the middle ear, which can cause the tympanic membrane to protrude (or retract), thereby resulting in adhesion, e.g., with the stapes. To counteract this, and to enable post-operative motions of the tympanic membrane to be emulated, the top plates of known ossicle prostheses are designed to be tiltable relative to the connecting element that connects the top plate with the second fastening element and is usually designed as a longitudinal shank. A top plate of this type, which is rigid yet tiltable relative to the connecting element is described, e.g., in US 2004/0162614 A1I, in the article M. W. YUNG, Ph.D., F.R.C.S., D.L.O., C. BREWIS, F.R.C.S., "A comparison of the user-friendliness of hydroxyapatite and titanium ossicular prostheses", The Journal of Laryngology & Otology, February 2002, Vol. 116, pp. 97-102, or, e.g., in US 2006/0271190 A1.

The disadvantage of these known ossicle prostheses, however, is that, due to the rigid tilting of the top plate that occurs when the tympanic membrane performs localized medial motions, the opposite side of the top plate is moved laterally outwardly, thereby resulting in pressure peaks on the tympanic membrane.

SUMMARY OF THE INVENTION

The object of the present invention, therefore, is to improve a generic device of the type described initially using the simplest technical means possible so that a high level of post-operative flexibility and variability of the prosthesis is attained in an uncomplicated and cost-favorable manner, while also greatly improving the quality of sound conduction through the prosthesis and preventing the complications described above from occurring.

According to the present invention, this object is attained in a surprisingly simple yet effective manner by providing the segment elements with a geometric design that allows them to locally emulate localized medial motions made by the tympanic membrane but to not transmit the motion to remote regions of the top plate. Due to this flexible design of the ossicle prosthesis, the entire top plate is prevented from tilting in a rigid manner when the tympanic membrane makes a slight medial motion of this type. Instead, the top plate winds inward on itself in a localized manner, while also transmitting any large surface-area motions of the tympanic membrane caused by sound to the connecting element, thereby ensuring that sound is transmitted in an optimal manner from the tympanic membrane toward the middle ear space.

The advantages of the known ossicle prosthesis described above, and as described in DE 20 2005 003 782 U1—which represents the general class—are therefore utilized in a simple manner, while also retaining the advantages of the prostheses described in US 2004/0162614 A1 and US 2006/0271190 A1 cited above, and avoiding all of the disadvantages of a rigid tilting of the top plate.

A particularly preferred embodiment of the inventive ossicle prosthesis is characterized by the fact that the segment elements have a maximum width b, the radially outer annular region has a maximum width B, and the following applies: 2b<B.

To attain the desired level of flexibility, given a maximum width b of the segment elements and a minimum diameter D of the top plate, including the annular region, the following should apply: b≦0.05D, preferably b≈0.03D. With the related art, e.g., with the ossicle prosthesis described in US 2004/0162614 A1, the ratio d/D is at least 0.1 or more.

It is also favorable when the top plate of the inventive ossicle prosthesis has a thickness, in particular a plate thickness t between 0.01 mm and 0.25 mm, a minimum diameter D between 2 mm and 5 mm, and the segment elements have a maximum width b between 0.01 mm and 0.2 mm.

According to particularly preferred embodiments of the present invention, the segment elements extend in the plane of the top plate not in a straight line, but along lines with several curves, thereby enhancing the desired effect of localized flexibility of the top plate, and ensuring that deflections are limited to a localized region when the tympanic membrane makes slight medial motions. In addition, the top plate is therefore able to more easily emulate any post-operative change in the tympanic membrane.

In further advantageous embodiments of the inventive ossicle prosthesis, every segment element is connected with at least two other segment elements, thereby producing a type of network of segment elements.

To increase the desired level of flexibility, with one class of embodiments, the segment elements may extend continuously between the centralized attachment region and the radially outer annular region.

As an alternative, however, at least a few of the segment elements may have a break between the central attachment region and the radially outer annular region.

Likewise, in a further class of embodiments of the present invention, the radially outer annular region may extend in a closed, continuous ring. As a result, when post-operative retractions occur, the formation of peaks directed toward the tympanic membrane may be prevented.

In contrast, with alternative embodiments of the inventive ossicle prosthesis, the radially outer annular region includes at least one break, and preferably several breaks.

As known per se from the related art, the radially outer annular region may be oval or circular in shape.

Alternative embodiments of the present invention with which the radially outer annular region has a serpentine outer contour may also be advantageous, however.

To simplify the surgical implantation of the inventive ossicle prosthesis, further embodiments may be characterized geometrically by the fact that the radially outer annular region includes a recess on one side for receiving the handle of the hammer.

With the inventive ossicle prosthesis, the top plate is typically located at one end of a longitudinal shank that connects the top plate with the other end of the ossicle prosthesis, as is well known from the related art.

To attain the flexibility and variability of the prosthesis described above, as described in EP 1 181 907 B1, with a particularly preferred embodiment, at least one ball joint is provided on or in the longitudinal shank. In terms of particularly high post-operative mobility of the prosthesis, an embodiment is particularly advantageous with which the longitudinal shank includes a large number of further rotary elements which abut each other, preferably in the form of a ball joint chain.

As an alternative, with particularly simple embodiments of the inventive prosthesis that may be manufactured in a cost-favorable manner, the shank may be designed as a single, continuous piece, which is rigid in particular.

The prosthesis will be designed according to the particular defect to be eliminated or at least ameliorated in terms of its effect on the patient via use of the inventive ossicle prosthesis. With all embodiments of the present invention, the first fastening element will include a top plate designed to rest on the tympanic membrane. With many embodiments, the prosthesis may be attached, e.g., to the limb of incus or to the stapes, or it may be inserted directly into the inner ear. In this context, an embodiment is advantageous with which the ossicle prosthesis is located at the end of the hammer (=umbo) or directly adjacent thereto, thereby attaining the greatest leverage for the mechanical transmission of the sound via motions in the artificial or natural ossicular chain.

One class of embodiments of the inventive ossicle prosthesis is characterized by the fact that the second fastening element is designed as a plate, a sleeve, a loop, as a closed bell, as a bell with one or two slots, or as a clip for mechanically connection with a further element of the ossicular chain.

In refinements of these embodiments, the prosthesis is fastened via the top plate to the tympanic membrane and via the second fastening element to the incus or stapes.

Alternative embodiments may provide that the ossicle prosthesis is coupled via its end on which the second fastening element is attached via perforation of the stapes (stapedectomy or stapedotomy), and/or by opening up the human cochlea (=cochleotomy), to which the top plate is attached at the opposite end, directly to the inner ear, using a plunger, in particular.

In addition to the post-operative shifting of position, a further problem results after ossicle prostheses are implanted: The middle ear of the human body may be described as a "half-open region". Any implantation material inserted in the body as part of the reconstruction of the middle ear and its structures experiences a particular stress that predominates in a contaminated and infected environment, and which typically attacks the material. Since the objective of implanting an ossicle prosthesis must always be to enable the implant to remain in the patient's middle ear for as long as possible without complications, a sustained attack on the material may result in damage to the prosthesis and/or a local infection. Neither of these consequences is tolerable. To permanently prevent damage to the implantation material or the surrounding tissue, with a further particularly preferred embodiment of the present invention, the surface of the ossicle prosthesis is coated entirely or at least in sections with a biologically active coating, in particular a growth-inhibiting and/or growth-promoting and/or antibacterial coating.

The top plate of the inventive ossicle prosthesis should always include a growth-promoting coating, but a second fastening element that leads directly into the inner ear, e.g., in the form of a plunger, should have a growth-inhibiting coating.

The inventive ossicle prosthesis itself or parts thereof can be made of titanium and/or gold and/or tantalum and/or steel, and/or an alloy of these metals. It is known that titanium, in particular, in addition to being stiff and having excellent sound-conducting properties, also exhibits excellent biocompatibility with the human ear.

In terms of the post-operative position adjustment described above, embodiments of the present invention are advantageous with which the prosthesis or parts thereof—in particular one of the fastening elements—are made of a material with memory effect or superelastic properties, Nitinol in particular, as is known, e.g., from WO 02/069850 A1 or U.S. Pat. No. 6,554,861 B2.

As an alternative or in addition thereto, with further embodiments, parts of the inventive ossicle prosthesis may be made of a ceramic material.

Embodiments of the present invention are also possible, with which the prosthesis or parts thereof are made of biocompatible plastics, particularly silicone, polytetrafluoroethylene (PTFE), or fibrous composite materials. With these materials, post-operative rejection reactions may also be prevented in most cases.

According to a particularly preferred embodiment of the inventive ossicle prosthesis, the mass distribution of the individual parts of the prosthesis is calculated depending on a desired, specifiable frequency response of sound conduction in the middle ear. This allows the sound propagation properties to be tuned to a certain extent using a custom-made ossicle prosthesis without a great deal of additional technical outlay.

With special embodiments, a tuning effect of this type can be attained, e.g., by fastening at least one additional mass to a part of the ossicular chain or the prosthesis depending on a desired, specifiable response of sound conduction in the middle ear. With advantageous refinements of these embodiments, the additional mass is fastened to a part of the ossicular chain or the prosthesis using a clip. The additional mass and/or clip may also be coated with a biologically active coating.

Finally, a further embodiment of the present invention is characterized by the fact that the prosthesis is connected with an active vibrating part of a hearing aid which is active and implantable, in particular. This also enables further hearing damage caused by the use of modern electronic devices to be prevented or at least ameliorated in terms of its effect, and a physical connection of the prosthesis with the outside world does not cause a problem—due to the coating described above, when the coating is antibacterial in design—that would result from the increased introduction of bacteria into the region of the middle ear.

Further features and advantages of the present invention result from the detailed description of exemplary embodiments of the invention presented below with reference to the figures in the drawing, which shows the details that are essential to the present invention. Further features and advantages of the present invention also result from the claims. The individual features can be realized individually, or they can be combined in any possible manner in different variations of the present invention.

Exemplary embodiments of the present invention are depicted in the schematic drawing and are described in greater detail in the description below.

DESCRIPTION OF THE PREFERRED EMBODIMENTS

Figure 1:
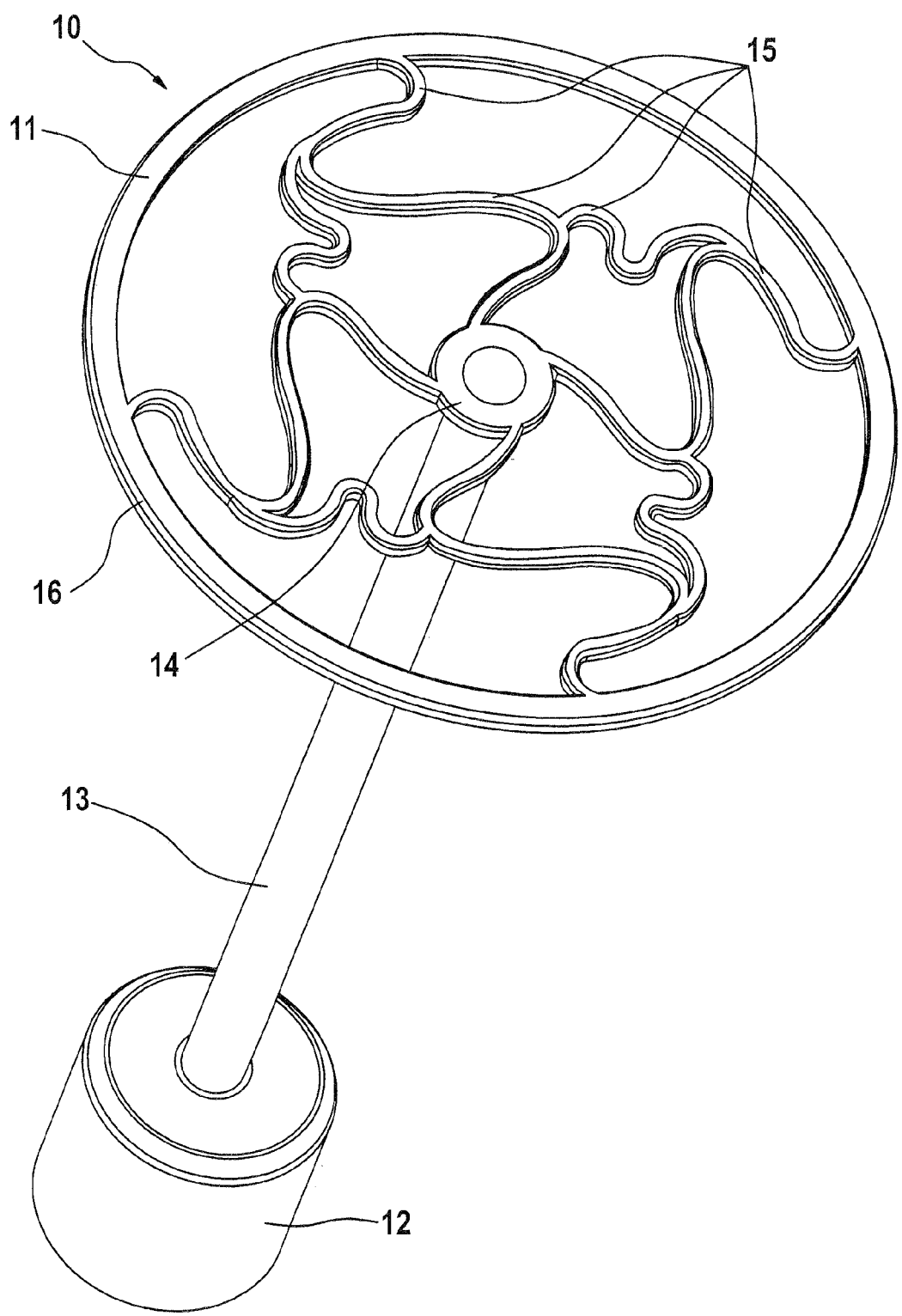
FIG. 1 shows a schematic, three-dimensional depiction of an embodiment of the inventive ossicle prosthesis with a plunger as the second fastening element on the other end of the longitudinal shank, in a top view of the top plate.

Ossicle prostheses 10; 20 depicted schematically in FIG. 1 include, at one end, a first fastening element 11; 21 that is designed as a top plate designed to rest on the tympanic membrane. Attached to the other end of ossicle prosthesis 10; 20 is a second fastening element 12; 22 for mechanically connecting the prosthesis with a component or parts of a component of the ossicular chain or with the inner ear. Located between the two is a connecting element 13; 23 that connects fastening elements 11, 12 and 21, 22 in a sound-conducting manner. In the embodiments shown, connecting element 13; 23 is a longitudinal shank.

In the embodiments depicted in the drawing, the top plates of ossicle prostheses 10; 20 are composed of a radially outward annular region 16; 26, a central attachment region 14; 24 for mechanically attaching the top plate to connecting element 13; 23, and several segment elements 15; 25 for radially connecting radially outer annular region 16; 26 with central attachment region 14; 24. According to the present invention, segment elements 15; 25 are geometrically designed such that they locally emulate any localized medial motions made by the tympanic membrane, but they do not transmit the motion to distant regions of the top plate.

In particular, with the embodiments shown, segment elements 15; 25 extend in the plane of the top plate not in a straight line, but along lines with several curves, and each segment element 15; 25 is connected with at least two other segment elements 15; 25. Segment elements 15; 25 have a maximum width b, and radially outer annular region (16; 26) has a maximum width B, with 2b<B. The top plates, including annular region 16; 26, have a minimum diameter D, with $b \leqq 0.05D$, and preferably $b \approx 0.03D$.

In the present exemplary embodiment, second fastening element 12 at the end—opposite to the top plate—of ossicle prosthesis 10 shown in FIG. 1—is designed as a plunger for use to attach ossicle prosthesis 10 directly to the inner ear.

Figure 2:
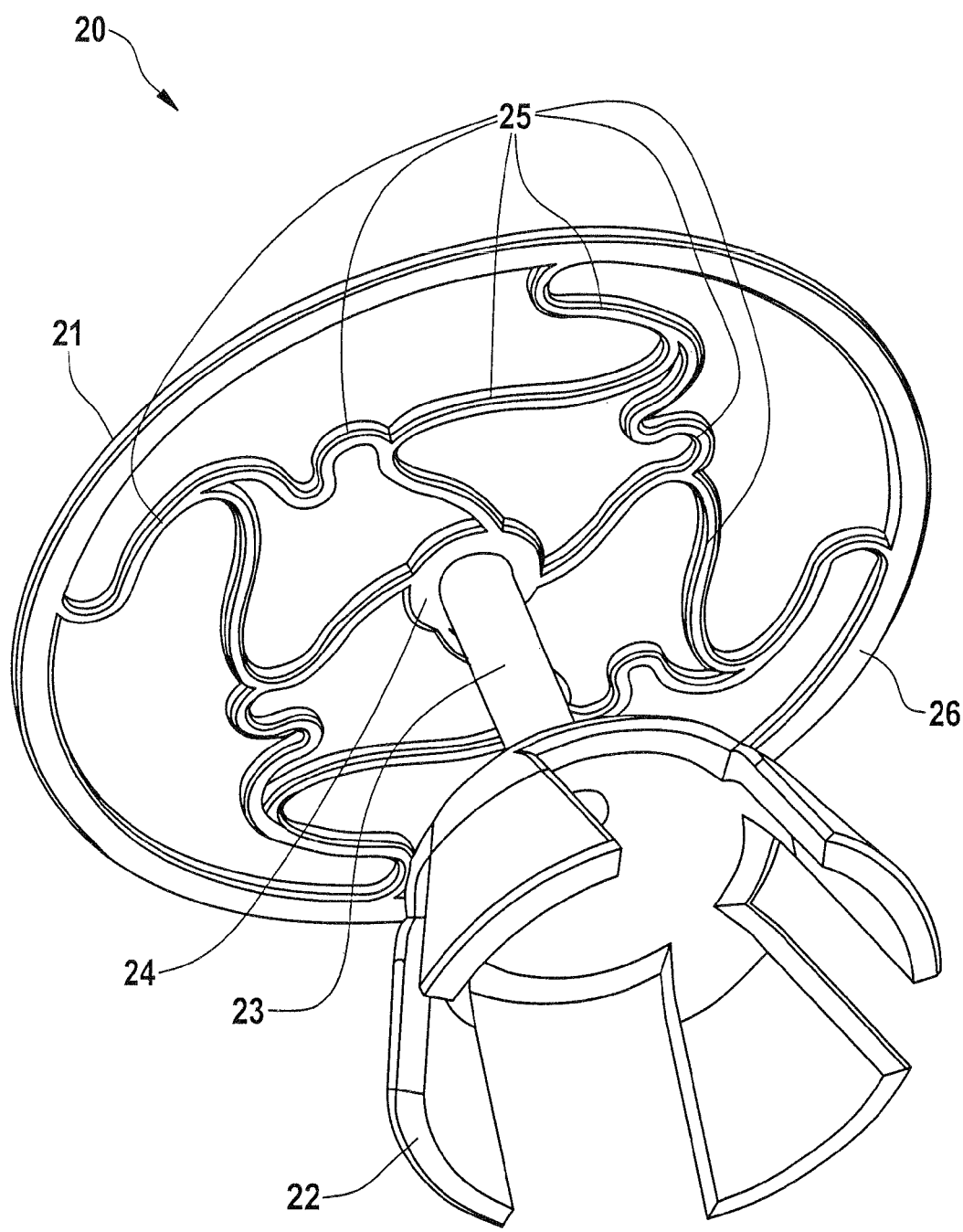
FIG. 2 shows an embodiment with a bell-shaped, second fastening element, in a view of the bell from the bottom up.

With the embodiment shown in FIG. 2, however, second fastening element 22 has a bell shape, and it serves to attach ossicle prosthesis 20 to a component of the ossicular chain, e.g., to the incus or the stapes.

The mass distribution of the individual parts of inventive ossicle prosthesis 10; 20 may be calculated depending on a desired, specifiable response of sound conduction in the middle ear, to allow the sound propagation properties to be tuned in an individualized manner.

In further embodiments of the inventive ossicle prosthesis which are not depicted separately in the drawing, the segment elements and/or the outer annular regions may have other geometries in order to attain the desired flexibility of the particular top plate. For example, at least a few of the segment elements may have a break between the central attachment region and the radially outer annular region. The radially outer annular region may also be designed with one or several breaks. The radially outer annular region may have a serpentine outer contour and/or a recess on one side for accommodating the handle of the hammer.

It will be understood that each of the elements described above, or two or more together, may also find a useful application in other types of constructions differing from the type described above.

While the invention has been illustrated and described as embodied in an ossicle prosthesis with sensitive top plate, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

The invention claimed is:

1. An ossicle prosthesis for replacing or bridging at least one component or parts of a component of an ossicular chain, comprising a first fastening element provided at one end and configured as a top plate for a mechanical connection with a tympanic membrane; a second fastening element provided at another end for a mechanical connection with a component or parts of a component of the ossicular chain or with an inner ear; and a connecting element that connects said fastening elements with each other in a sound-conducting manner and configured as a longitudinal shank between said fastening elements substantially perpendicular to said fastening elements, said top plate including a radially outer annular region, a radially inner attachment region for mechanically attaching said top plate to said connecting element, and several curvilinear segment elements for radially connecting said radially outer annular region with said radially inner attachment region, said curvilinear segment elements being geometrically configured such that they do not transmit any localized medial motions of the tympanic membrane due to post-operative forces to distant regions of said top plate.

2. An ossicle prosthesis as defined in claim 1, wherein said segment elements have a maximum width b, and said radially outer annular region has a maximum width B, selected in accordance with the following ratio: $2b<B$.

3. An ossicle prosthesis as defined in claim 1, wherein said segment elements have a maximum width b, and said top plate, including said radially outer annular region, has a maximum diameter D selected in accordance with the following ratio:

$$b \leq 0.05D.$$

4. An ossicle prosthesis as defined in claim 3, wherein said ratio between the maximum width d of the segment elements and the minimum diameter D of said top plate including said radially outer annular region is $b \approx 0.03D$.

5. An ossicle prosthesis as defined in claim 1, wherein said top plate has a plate thickness t between 0.01 mm and 0.25 mm and a minimum diameter D between 2mm and 5 mm, and said segment elements have a maximum width b between 0.01 mm and 0.2 mm.

6. An ossicle prosthesis as defined in claim 1, wherein said segment elements extend in a plane of said top plate not in a straight line, but along lines with several curves.

7. An ossicle prosthesis as defined in claim 1, wherein each of said segment elements is connected with at least two other of said segment elements.

8. An ossicle prosthesis as defined in claim 1, wherein said segment elements extend continuously between said radially inner attachment region and said radially outer annular region.

9. An ossicle prosthesis as defined in claim 1, wherein at least a few of said segment elements have a break between said radially inner attachment region and said radially outer annular region.

10. An ossicle prosthesis as defined in claim 1, wherein said radially outer annular region extends in a closed, continuous ring.

11. An ossicle prosthesis as defined in claim 1, wherein said radially outer annular region includes at least one break.

12. An ossicle prosthesis as defined in claim 1, wherein said radially outer annular region includes several breaks.

13. An ossicle prosthesis as defined in claim 1, wherein said radially outer annular region has a circular shape.

14. An ossicle prosthesis as defined in claim 1, wherein said radially outer annular region has a serpentine outer contour.

15. An ossicle prosthesis as defined in claim 1, wherein said radially outer annular region includes a recess on one side for accommodating a handle of a hammer.

16. An ossicle prosthesis as defined in claim 1, wherein said longitudinal shank includes at least one joint.

17. An ossicle prosthesis as defined in claim 16, wherein said at least one joint of said longitudinal shank is a ball joint.

18. An ossicle prosthesis as defined in claim 1, wherein said longitudinal shank includes a ball joint chain.

19. An ossicle prosthesis as defined in claim 1, wherein said longitudinal shank is configured as a one continuous piece which is rigid.

20. An ossicle prosthesis as defined in claim 1, wherein said second fastening element is configured as a clip for mechanical connection with a further component of the ossicular chain.

21. An ossicle prosthesis as defined in claim 1; and further comprising means for fastening the ossicle prosthesis to the tympanic membrane at one end and to stapes at the other end.

22. An ossicle prosthesis as defined in claim 1, wherein the ossicle prosthesis is attachable via perforation of a base of stapes by stapedectomy or stapedotomy, to which said top plate is attached at an opposite end directly to the inner ear, using a plunger in particular.

23. An ossicle prosthesis as defined in claim 1, wherein the ossicle prosthesis or parts thereof are composed of a material selected from the group consisting of a biocompatible plastic and a fibrous composite material.

24. An ossicle prosthesis as defined in claim 23, wherein said biocompatible plastic is selected from the group consisting of silicone and polytetrafluorethylene while said fibrous composite material is composed of carbon fibers.

25. An ossicle prosthesis as defined in claim 1, wherein parts of the ossicles prosthesis are composed of a material selected from the group consisting of titanium, gold, tantalum, and an alloy thereof.

26. An ossicle prosthesis as defined in claim 1, wherein parts of the ossicle prosthesis are composed of a material with memory effect.

27. An ossicle prosthesis as defined in claim 26, wherein the material with memory effect of the parts of the ossicle prosthesis is Nitinol.

28. An ossicle prosthesis as defined in claim 1, wherein parts of the ossicle prosthesis are composed of a ceramic material.

29. An ossicle prosthesis as defined in claim 1; and further comprising a biologically active coating which covers the ossicle prosthesis at least in sections.

30. An ossicle prosthesis as defined in claim 29, wherein said biological active coating is a coating selected from the group consisting of a growth-inhibiting coating, a growth-promoting coating, an antibacterial coating, and a combination thereof.

31. An ossicle prosthesis as defined in claim 1, wherein said top plate includes a growth-promoting coating.

32. An ossicle prosthesis as defined in claim 1, wherein said second fastening element is a piston that includes a growth-inhibiting coating.

33. An ossicle prosthesis as defined in claim 1, wherein individual parts of the ossicle prosthesis are configured so that their mass distribution depends on a desired, specifiable frequency response of sound conduction in the middle ear.

34. An ossicle prosthesis as defined in claim 1; and further comprising at least one additional mass, which depends on a desired, specifiable frequency response of sound conduction in the middle ear, and is fastened to the ossicle prosthesis or to a part of the ossicular chain, using a clip in particular.

35. An ossicle prosthesis as defined in claim 1; and further comprising means for connecting the ossicle prosthesis with an active vibration part of a hearing aide which is active and implantable in particular.

36. An ossicle prosthesis as defined in claim 1, wherein parts of the ossicle prosthesis are composed of metal.

37. An ossicle prosthesis as defined in claim 1, wherein said radially outer region has an oval shape.

38. An ossicle prosthesis as defined in claim 1, wherein said second fastening element is configured as an element selected from the group consisting of a plate, a sleeve, a loop, a closed bell, and a bell with one or two slots.

39. An ossicle prosthesis as defined in claim 1, wherein the ossicle prosthesis is attachable by opening up a human cochlea by cochleotomy, to which said top plate is attached at an opposite end directly to the inner ear, using a plunger in particular.

* * * * *